(12) United States Patent
Wiley

(10) Patent No.: US 7,201,574 B1
(45) Date of Patent: Apr. 10, 2007

(54) METHOD FOR MEASURING ORTHODONTIC ARCH WIRES

(76) Inventor: Steven M. Wiley, 348 Vegas Dr., Las Vegas, NV (US) 89108

( * ) Notice: Subject to any disclaimer, the term of this patent is extended or adjusted under 35 U.S.C. 154(b) by 0 days.

(21) Appl. No.: 11/290,377

(22) Filed: Nov. 30, 2005

(51) Int. Cl.
*A61C 3/00* (2006.01)
*A61C 19/04* (2006.01)

(52) U.S. Cl. .............................. 433/3; 433/24; 433/27

(58) Field of Classification Search ................ 433/2–3, 433/20, 24, 72; 33/513–514, DIG. 7, DIG. 13; 606/102
See application file for complete search history.

(56) References Cited

U.S. PATENT DOCUMENTS

| | | | |
|---|---|---|---|
| 2,705,367 A * | 4/1955 | Berke ............................. 433/8 |
| 3,581,400 A * | 6/1971 | Snead ............................. 433/4 |
| 3,906,634 A * | 9/1975 | Aspel ............................ 433/24 |
| 3,916,526 A * | 11/1975 | Schudy ........................... 433/8 |
| 4,983,120 A * | 1/1991 | Coleman et al. .............. 433/24 |
| 6,722,878 B2 * | 4/2004 | Graham .......................... 433/3 |
| 6,736,637 B2 * | 5/2004 | Bond ............................ 433/20 |

* cited by examiner

*Primary Examiner*—John J Wilson
(74) *Attorney, Agent, or Firm*—Harry M. Weiss; Jeffrey Weiss; Weiss & Moy, P.C.

(57) ABSTRACT

A method for measuring arch wires. A guide wire is provided, having at one end an exposed length of wire and a stop. The exposed length of wire may be inserted into a buccal tube, up to the stop. At least a portion of the guide wire may then be inserted into brackets, at least to a point proximate a midpoint of the patient's teeth. The midpoint may be marked on the guide wire, for example by clamping. The guide wire may then be removed, and compared to an arch wire. The arch wire may then be cut to length, outside of the patient's mouth, and thereafter installed in the conventional manner.

11 Claims, 5 Drawing Sheets

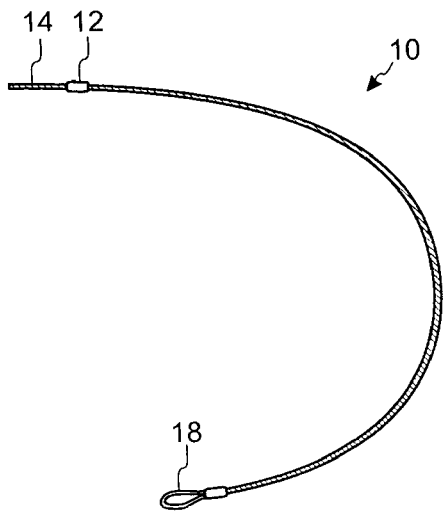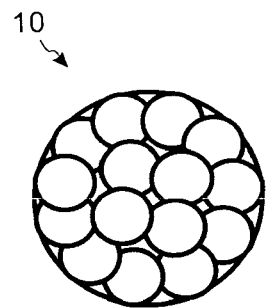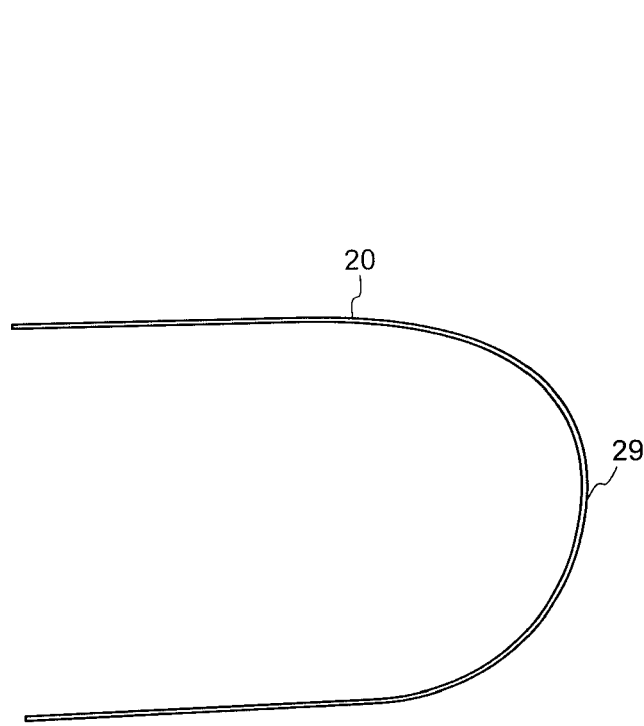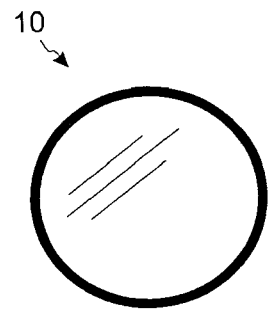
Fig. 1
Fig. 1A
Fig. 1B
Fig. 2

METHOD FOR MEASURING ORTHODONTIC ARCH WIRES

FIELD OF THE INVENTION

The present invention relates to the field of orthodontia and, more particularly, to a method for measuring arch wires.

BACKGROUND OF THE INVENTION

The use of braces to move teeth and/or change jaw shape is, of course, well-known. The components of typical braces include: (a) brackets, which are typically attached to the teeth and which serve as a means of fastening the arch wire: (b) an arch wire, a metal wire which is attached to the brackets to move the teeth; and (c) a buccal (or molar) tube, a small metal part which is welded on the outside of a molar bank and which contains a slot to hold, among other things, the arch wire.

Upon the installation of the braces, and during periodic tightening of installed braces, it is necessary to install the arch wire. Typically, this occurs by the installation of the wire into position, with the orthodontist inserting a cutting implement into the mouth of the patient and cutting off excess wire length at a point that is distal to the buccal tube.

A need exists for an improved method of cutting an arch wire to length, which preferably does not require that the cutting step occur inside of the mouth of the patient. The present invention satisfies these needs and provides other, related, advantages.

SUMMARY OF THE INVENTION

In accordance with an embodiment of the present invention, a method for measuring arch wires is disclosed. The method comprises the steps of: providing a guide wire comprising a stop located proximate a first end thereof and an exposed section of wire distal to the stop; wherein the exposed section of wire is insertable into a buccal tube, to a point whereby the stop contacts the buccal tube; inserting the exposed section of wire into the buccal tube, to the point that the stop contacts the buccal tube; placing the guide wire into brackets, to a point proximate a midpoint of a patient's teeth; marking the midpoint on the guide wire; removing the guide wire from the brackets and buccal tube; comparing the marked guide wire to a length of arch wire; determining an appropriate length of the arch wire based on such comparison; and cutting the arch wire to the appropriate length.

In accordance with another embodiment of the present invention, a method for measuring arch wires is disclosed. The method comprises the steps of: providing a guide wire comprising a stop located proximate a first end thereof and an exposed section of wire distal to the stop; wherein the exposed section of wire is insertable into a buccal tube, to a point whereby the stop contacts the buccal tube; wherein the guide wire further comprises a loop at a second end thereof; inserting the exposed section of wire into the buccal tube, to the point that the stop contacts the buccal tube; placing the guide wire into brackets, to a point proximate a midpoint of a patient's teeth; marking the midpoint on the guide wire by clamping the midpoint; removing the guide wire from the brackets and buccal tube; comparing the marked guide wire to a length of arch wire; determining an appropriate length of the arch wire based on such comparison; and cutting the arch wire to the appropriate length.

BRIEF DESCRIPTION OF THE DRAWINGS

FIG. 1 is a top view of a guide wire, which may be used to practice an embodiment of the method of the present invention.

FIG. 1A is a cross-sectional view of a guide wire consistent with an embodiment of the present invention, wherein the guide wire is comprised of braided steel.

FIG. 1B is a cross-sectional view of a guide wire consistent with an embodiment of the present invention, wherein the guide wire is comprised of a non-braided material.

FIG. 2 is an arch wire, which may be used to practice an embodiment of the method of the present invention.

DETAILED DESCRIPTION OF THE PREFERRED EMBODIMENTS

Figure 3:
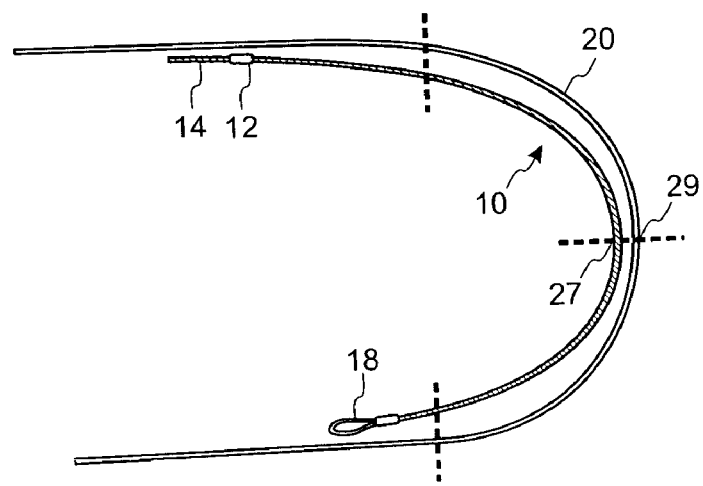
FIG. 3 illustrates the guide wire of FIG. 1 in relation to the arch wire of FIG. 2.

Referring first to FIGS. 1, 1A, 3 and 4–4B, a guide wire 10 utilizable in an embodiment of the method of the present invention is shown. The guide wire 10 preferably has a stop 12 proximate a first end thereof. The stop 12 is intended to permit an exposed end 14 of the guide wire 10 to be installed within a buccal tube 16, but to then prevent any further insertion of the guide wire 10.

At a second end of the guide wire 10, it is preferred to provide a loop 18. The purpose of the loop 18 is to prevent the uninstalled end of the guide wire 10 from poking a patient's lip and/or gums. It should be noted that, while not preferred, it would be possible to provide a guide wire 10 without loop 18.

Referring specifically to FIGS. 1A and 1B, the guide wire 10 may be a copper NiTi wire, braided stainless steel, or may be comprised from other desired material(s), including either metal or plastic. Since the guide wire 10 does not remain in the mouth of the patient, it may be possible to utilize in the construction of the guide wire 10 materials that would not be suitable for incorporation into a person's braces.

A length of arch wire 20 having a midpoint 29 is shown in FIGS. 2 and 3. The arch wire 20 may be a typical, prior art arch wire.

Figure 4:
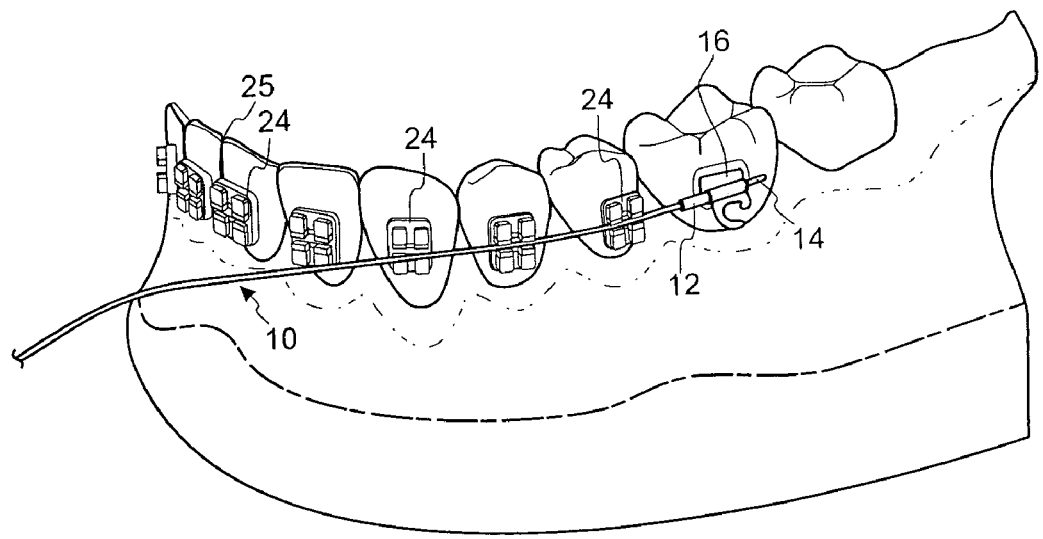
FIG. 4 illustrates a step in the installation of a guide wire onto a patient's brackets.
Figure 5:
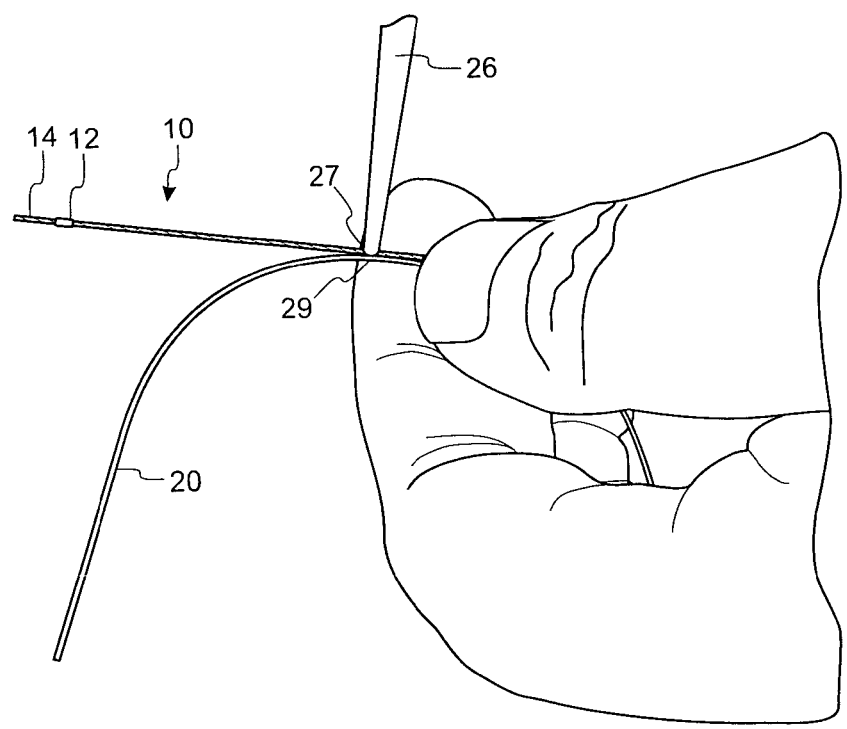
FIG. 5 illustrates a step in an embodiment of the method of the present invention, with the clamped midpoint of the guide wire being positioned against a length of arch wire.
Figure 6:
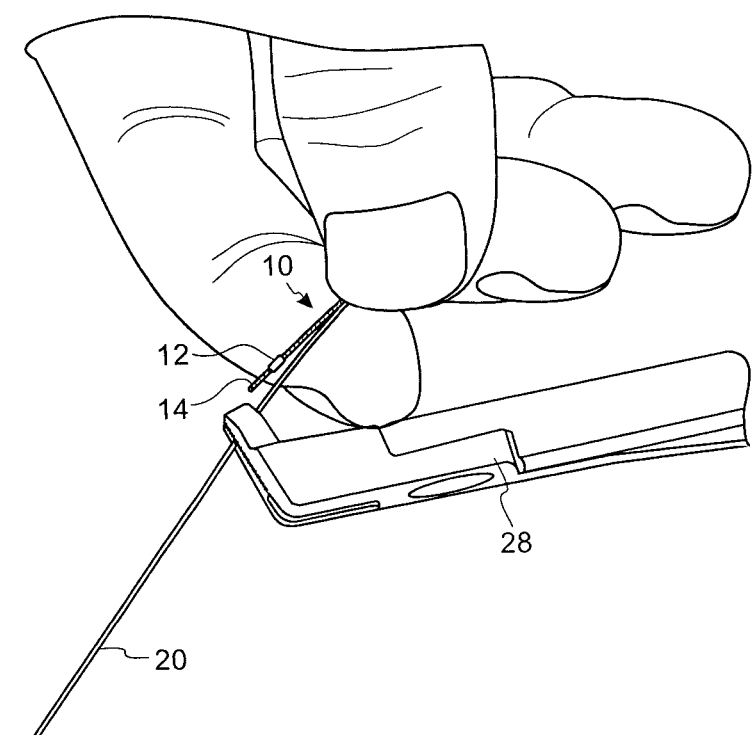
FIG. 6 illustrates a step in an embodiment of the method of the present invention, showing a cutting of the length of arch wire.

Referring now to FIGS. 4–6, steps in a method for measuring an arch wire 20 consistent with an embodiment of the present invention are shown. As shown in FIG. 4, the exposed end 14 of the guide wire 10 is inserted into the buccal tube 16. Insertion continues until the stop 12 contacts the buccal tube 16, preventing further distal travel of the guide wire 10.

Figure 4A:
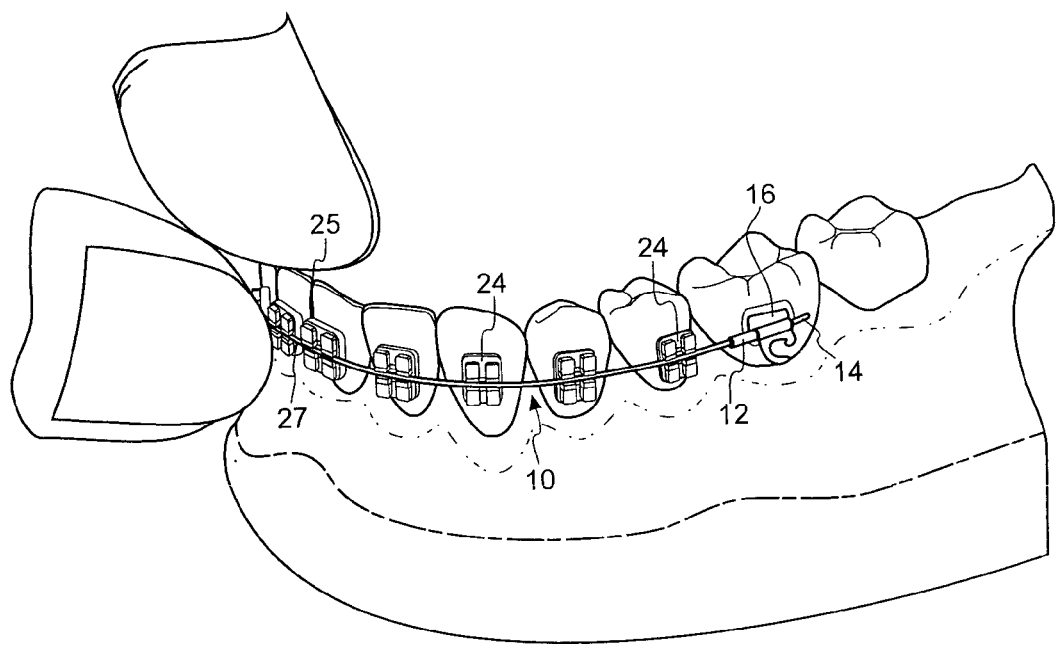
FIG. 4A illustrates another step in the installation of a guide wire onto a patient's brackets.

As shown in FIGS. 4 and 4A, the guide wire 10 is then placed through the slots of the patient's brackets 24. This installation need only continue until the guide wire 10 has been installed to a mid-point 25 of the patient's mouth—as best seen in FIG. 4A. In other words, installation need only occur on the brackets 24 on a first side of the patient's mouth.

Figure 4B:
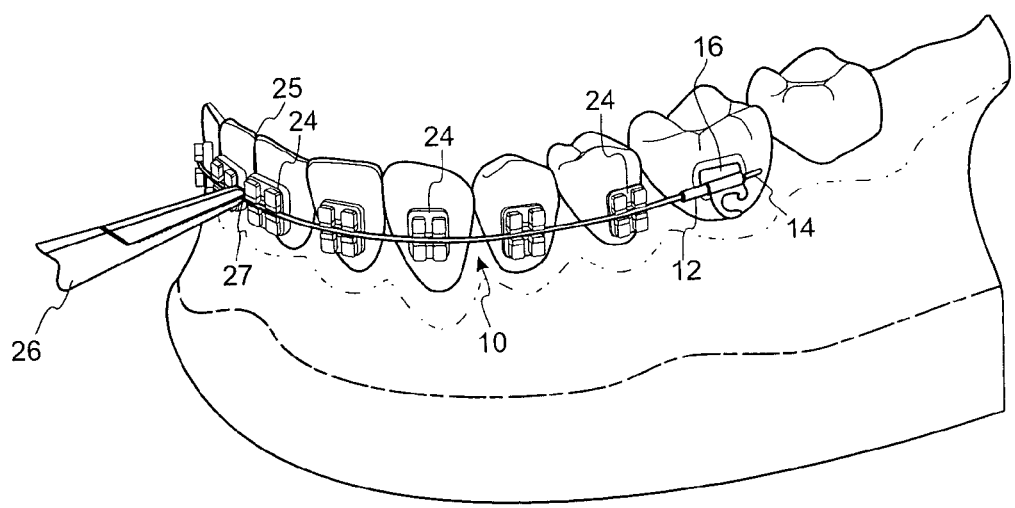
FIG. 4B illustrates a step in an embodiment of the method of the present invention, with a guide wire in position on a patient's brackets and buccal tube.

As shown in FIG. 4B, when installation of the guide wire is at or slightly beyond the midpoint 25, the practitioner may clamp—utilizing clamp 26—a point establishing the midpoint 27 of the guide wire 10. This midpoint 27 is the presumed midpoint of the arch wire 20, when properly cut to length. The guide wire is then removed from the patient's mouth, with the clamp 26 still in place.

It should be noted that, as an alternative to the use of a clamp 26, it would also be possible to cut, crease, alter, mark or otherwise act upon the guide wire 10, so as to establish the midpoint 27.

As shown in FIG. 5, the clamped (or otherwise marked) guide wire 10 is then positioned proximate an arch wire 20 that needs to be cut to length—with a midpoint 29 of the arch wire 20 positioned against a midpoint 27 of the guide wire 10. In such manner as shown in FIG. 6, a desired endpoint of the arch wire 20 is noted. Utilizing a suitable cutting implement 28, the excess on the second end of the arch wire 20 may then be cut.

Typically, a patient's teeth will be symmetrical, such that establishing the length of a first side of the patient's mouth to the midpoint 25 will be sufficient to establish the total length of arch wire 20 that is required. However, in the event that a patient's mouth is asymmetrical, measurement to the midpoint 25 utilizing the guide wire 10 will need to be performed twice—once on each side of a patient's mouth—in order to determine the proper length of the arch wire 20.

It should be reiterated that these comparison and cutting steps occur outside of the patient's mouth. This makes the cutting process easier for practitioner and patient alike. It also makes the cutting process more precise.

Figure 7:
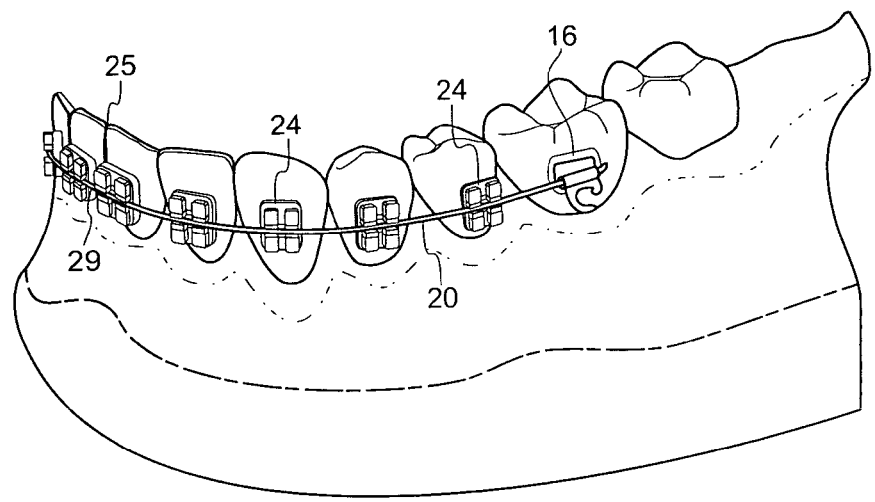
FIG. 7 illustrates a step in an embodiment of the method of the present invention, illustrating an installed arch wire.
Figure 7A:
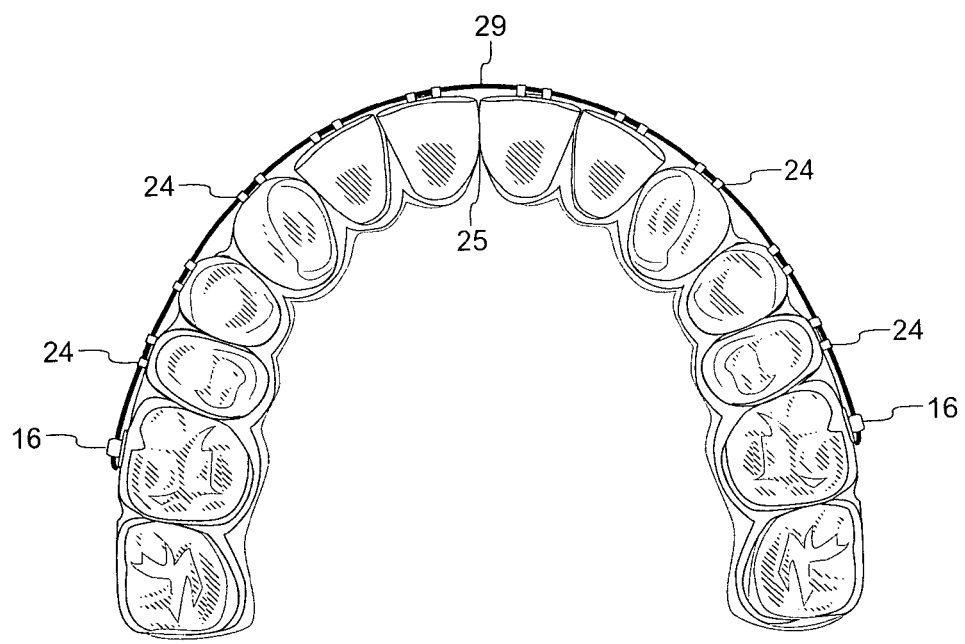
FIG. 7A illustrates an installed arch wire.

The cut-to-size arch wire 20 may then be installed in the typical manner, with no further cutting steps required. As shown in FIGS. 7 and 7A, it is preferred to bend the exposed end of arch wire 20 toward the inside of the patient's mouth to prevent injury to the patient's cheek, which bending step is typically accomplished utilizing a pair of pliers.

While various embodiments of the present invention are shown and described herein, it should be understood that variations may be possible without departing from the spirit or scope of the present invention.

I claim:

1. A method for measuring arch wires comprising the steps of:
   providing a guide wire comprising a stop located proximate a first end thereof and an exposed section of wire distal to the stop;
   wherein the exposed section of wire is insertable into a buccal tube, to a point whereby the stop contacts the buccal tube;
   inserting the exposed section of wire into the buccal tube, to the point that the stop contacts the buccal tube;
   placing the guide wire into brackets, to a point proximate a midpoint of a patient's teeth;
   marking the midpoint on the guide wire;
   removing the guide wire from the brackets and buccal tube;
   comparing the marked guide wire to a length of arch wire;
   determining an appropriate length of the arch wire based on such comparison; and
   cutting the arch wire to the appropriate length.

2. The method of claim 1, wherein the guide wire comprises copper NiTi wire.

3. The method of claim 1, wherein the guide wire comprises braided stainless steel.

4. The method of claim 1, wherein the guide wire comprises plastic material.

5. The method of claim 1, wherein the guide wire further comprises a loop at a second end thereof.

6. The method of claim 1, wherein the marking step is performed by clamping the midpoint.

7. The method of claim 1, wherein the marking step is performed by cutting the guide wire.

8. A method for measuring arch wires comprising the steps of:
   providing a guide wire comprising a stop located proximate a first end thereof and an exposed section of wire distal to the stop;
   wherein the exposed section of wire is insertable into a buccal tube, to a point whereby the stop contacts the buccal tube;
   wherein the guide wire further comprises a loop at a second end thereof;
   inserting the exposed section of wire into the buccal tube, to the point that the stop contacts the buccal tube;
   placing the guide wire into brackets, to a point proximate a midpoint of a patient's teeth;
   marking the midpoint on the guide wire by clamping the midpoint;
   removing the guide wire from the brackets and buccal tube;
   comparing the marked guide wire to a length of arch wire;
   determining an appropriate length of the arch wire based on such comparison; and
   cutting the arch wire to the appropriate length.

9. The method of claim 8, wherein the guide wire comprises copper NiTi wire.

10. The method of claim 8, wherein the guide wire comprises braided stainless steel.

11. The method of claim 8, wherein the guide wire comprises plastic material.

* * * * *